United States Patent
Kamat et al.

(10) Patent No.: US 10,716,702 B2
(45) Date of Patent: Jul. 21, 2020

(54) APPARATUS FOR PLANTAR FOOT PAIN TREATMENT

(71) Applicants: Ehan Vinay Kamat, St. Louis, MO (US); Vinay Gopal Kamat, St. Louis, MO (US)

(72) Inventors: Ehan Vinay Kamat, St. Louis, MO (US); Vinay Gopal Kamat, St. Louis, MO (US)

(*) Notice: Subject to any disclaimer, the term of this patent is extended or adjusted under 35 U.S.C. 154(b) by 157 days.

(21) Appl. No.: 15/732,654

(22) Filed: Dec. 8, 2017

(65) Prior Publication Data

US 2018/0104095 A1    Apr. 19, 2018

Related U.S. Application Data

(63) Continuation-in-part of application No. 14/544,704, filed on Feb. 9, 2015, now abandoned.

(60) Provisional application No. 61/966,656, filed on Feb. 27, 2014.

(51) Int. Cl.
| | |
|---|---|
| *A61F 7/02* | (2006.01) |
| *A61F 7/10* | (2006.01) |
| *A61H 15/02* | (2006.01) |
| *A61H 15/00* | (2006.01) |
| *A61F 7/00* | (2006.01) |

(52) U.S. Cl.
CPC .............. *A61F 7/0241* (2013.01); *A61F 7/10* (2013.01); *A61H 15/02* (2013.01); *A61F 2007/0045* (2013.01); *A61F 2007/0219* (2013.01); *A61F 2007/108* (2013.01); *A61H 2015/0007* (2013.01); *A61H 2015/0014* (2013.01); *A61H 2201/0214* (2013.01); *A61H 2201/0257* (2013.01); *A61H 2201/1284* (2013.01); *A61H 2205/12* (2013.01)

(58) Field of Classification Search
CPC ............ A61H 15/00–02; A61H 1/0266; A61F 7/0241; A61F 2007/0219; A61F 2007/022–0223; A61F 2007/0257; A61F 2007/108; A61F 2007/0045
See application file for complete search history.

(56) References Cited

U.S. PATENT DOCUMENTS

| | | | |
|---|---|---|---|
| 85,749 A | 1/1869 | Mellor | |
| 181,836 A | 9/1876 | Graham | |
| 2,604,091 A * | 7/1952 | Hansen | ............... A61H 15/00 601/63 |
| 3,035,570 A | 5/1962 | Nelson | |
| 3,842,453 A | 10/1974 | Redfield | |
| 4,014,325 A | 3/1977 | Clarke | |
| 4,109,649 A | 8/1978 | Iyomasa | |
| D253,373 S | 11/1979 | Celeste | |
| 4,378,007 A | 3/1983 | Kachadourian | |
| 4,380,231 A | 4/1983 | Rocha et al. | |
| 4,538,806 A | 9/1985 | Wilkerson | |

(Continued)

*Primary Examiner* — Valerie L Woodward
(74) *Attorney, Agent, or Firm* — Paul M. Denk

(57) ABSTRACT

A device for applying cold therapy to the plantar surface the foot is disclosed. The device includes a base that provides reasonable stability for the device when applied to a supporting surface, such as the floor, and a removable, freezable roller. The roller is of sufficient width to encompass the entire plantar surface through a rolling motion. The user rolls the sole of his foot against the cold roller surface resulting in relief of common plantar ailments including plantar fasciitis.

7 Claims, 3 Drawing Sheets

(56) References Cited

U.S. PATENT DOCUMENTS

| | | |
|---|---|---|
| 4,627,618 A | 12/1986 | Schwartz |
| 4,720,098 A | 1/1988 | Gordon |
| 4,910,978 A | 3/1990 | Gordon et al. |
| 5,056,778 A | 10/1991 | Hull et al. |
| 5,131,383 A | 7/1992 | Juarez |
| 5,251,620 A | 10/1993 | Boucher et al. |
| 5,411,470 A | 5/1995 | Liptak et al. |
| 5,558,625 A * | 9/1996 | McKay ............... A61H 15/00 601/118 |
| 5,830,161 A | 11/1998 | Cosmano |
| 6,071,253 A | 6/2000 | Rivera |
| 6,129,687 A | 10/2000 | Powell et al. |
| 6,258,048 B1 | 7/2001 | Montague |
| 6,499,485 B1 | 12/2002 | Pepera |
| 6,565,522 B1 | 5/2003 | Chen |
| 6,793,636 B1 | 9/2004 | Pepera |
| 7,112,178 B1 | 9/2006 | Roozenburg |
| 2004/0210175 A1 | 10/2004 | Robbins |
| 2005/0049532 A1 | 3/2005 | Lee |
| 2007/0129654 A1 * | 6/2007 | Anderson, Jr. ........ A61H 15/00 601/119 |
| 2008/0154162 A1 | 6/2008 | Thiebaut |
| 2011/0245741 A1 | 10/2011 | L'Homme |
| 2012/0265106 A1 * | 10/2012 | Accardo ............ A61H 15/0092 601/15 |
| 2013/0197405 A1 * | 8/2013 | Williams, III ..... A61H 15/0092 601/19 |
| 2014/0142479 A1 | 5/2014 | Kaur et al. |
| 2014/0316314 A1 * | 10/2014 | Schubert ............... A61H 9/0078 601/149 |
| 2015/0133271 A1 * | 5/2015 | Jones .................... A61H 15/00 482/51 |
| 2015/0257969 A1 * | 9/2015 | Shannon ................ A61H 15/00 601/121 |

* cited by examiner

APPARATUS FOR PLANTAR FOOT PAIN TREATMENT

CROSS REFERENCE TO RELATED APPLICATION

This application is a continuation-in-part of the application having Ser. No. 14/544,704, filed on Feb. 9, 2015, which non-provisional patent application claims priority to the provisional application having Ser. No. 61/966,656, filed on Feb. 27, 2014.

FIELD OF THE INVENTION

This invention relates generally to an apparatus for the treatment of plantar fasciitis, and other foot ailments, and more particularly relates to an apparatus that is used to apply cold therapy in the treatment of common plantar foot ailments, including plantar fasciitis and tendonitis, through the application of a stabilized pivotal freezable roller applied to a base and which allows the user to roll the treated foot against a cold surface to furnish relief from pain.

BACKGROUND OF THE INVENTION

As everyone knows, the feet are susceptible to aliments that can disable even the most agile and athletic. In addition, as one grows old, the back part of the foot, in the region of the heel, can develop plantar fasciitis, which can not only be painful, but actually prevent one from normal walking. Such an ailment has even disabled the greatest of athletes, preventing them from participating in the sports they normally excel, with disastrous results to the team.

The feet are susceptible to stresses as they bear the weight of the body. Tendons of the foot are very susceptible to inflammatory injury secondary to standing, walking and running. Inflammation of a tendon is termed tendonitis and can be caused by repetitive sports activities, trauma, obesity, aging, and flat feet or high arches cause a common ailment. The plantar fascia is located in the arch of the foot and runs across the bottom of the foot spreading from the heel to the ball of the foot and is as wide as the width of the foot. The plantar fascia is a thick fibrous band of connective tissue that originates on the heel bone or calcaneus and extends along the sole of the foot towards the toes while supporting the arch of the foot. The plantar fascia serves to absorb stresses suffered by the foot and maintains the shape of the arch. If the tension on the plantar fascia becomes excessive then the plantar fascia my become inflamed or damaged causing a condition known as plantar fasciitis (PF). PF is a painful medical condition thought to be due to repetitive micro-tears of the plantar fascia.

Approximately ten percent of the population has PF in their lifetime. Approximately two million patients a year are treated for this condition. PF is usually felt on the underside of the heel and is worse with the first few steps of the day. Risk factors include obesity, high arches and repetitive impact activity such as running or sports.

This invention relates to the treatment of plantar fasciitis. More than 90% of patients will improve with conservative non-surgical treatment. Conservative treatments include rest and courses of non-steroidal anti-inflammatory medications such as ibuprofen or naproxen. Sometimes, with minor pain, particularly upon arising in the morning, stretching the leg forwardly, at the ankle, can sometimes relieve the minor pain of fasciitis. Where the pain may be more sustaining and acute, another accepted treatment for PF is freezing a water bottle and having the patient roll his foot over it for twenty minutes up to four times a day. The theory behind this widely used treatment is that PF pain is caused by micro-tears in the plantar fascia and that the use of ice alleviates and helps repair such tears. Frozen water bottles by their nature are not ideal to treat plantar fasciitis as they are susceptible to rupture and may vary in the degree of their effectiveness dependent upon the surface upon which they are rolled.

Other cold therapy treatment methods have been described in the prior art. By way of example, the United States patent to Roozenburg, U.S. Pat. No. 7,112,178, describes a Cold Therapy Foot Massager that utilizes a freezable core "dumbbell" type of foot massager, which can be rolled upon the ground. It may be effective, but it would appear to be rather clumsy of usage, and does not furnish an overall stabile device that one can use stationarily, to roll the foot upon.

The patent to Gordon, et al, U.S. Pat. No. 4,910,978, shows a Reusable Soft Fabric Cold Compress. This device does contain a gel, which may be subject to low temperature, before it is then applied to the patient's body.

Another temperature sensitive massager may be seen in the U.S. Pat. No. 5,251,620, to Boucher, et al, upon a Heat Massager, which is identified as a foot massager, of the heat massager type. It can be soaked in hot water, sunlight, or even in the range, in order to elevate its temperature before usage.

Other structural forms of foot treating or massaging devices can be seen in the United States patent to Nelson, U.S. Pat. No. 3,035,570, disclosing a Foot Treating Device.

A form of Unique Mechanical Foot Massager can be seen in the patent to Clarke, U.S. Pat. No. 4,014,325. It apparently operates upon the principle of a cylindrical member that the foot may impress upon, as it rolls on the floor.

The patent to Iyomasa, U.S. Pat. No. 4,109,649, shows another form of Foot Massager with a series of staggered projections that impress upon the under surface of the foot.

The patent to Celeste, No. Des. 253,373, shows a design for another type of Foot Massage Roller.

U.S. Pat. No. 4,378,007, to Kachadourian, shows another Massaging Device.

There are various other exercising dumbbells like devices, as can be seen in the Wilkerson U.S. Pat. No. 4,538,806, upon an Exerciser Dumbbells.

The patent to Schwartz, U.S. Pat. No. 4,627,618, shows an Aerobic Hand Weights.

The patent to Gordon, U.S. Pat. No. 4,720,098, shows another Exerciser with Beverage Reservoir.

The patent to Hull, et al, U.S. Pat. No. 5,056,778, shows a Liquid Filled Dumbbell.

Another Foot Massage Device is shown in the U.S. Pat. No. 5,131,383, in the patent to Juarez. Once again, the usage of this type of device requires that the user have something to hold onto, while making use of it, and trying to roll this device under foot.

The same is true with respect to the Foot Massager shown in U.S. Pat. No. 5,411,470, to Liptak, et al.

Another complex type of foot massager is shown in the U.S. Pat. No. 5,830,161, to Cosmano, upon an Alternating Ribbed Foot Massager. This device even incorporates an electrically operative vibrator, within its structure.

A Rollable Massaging Device is shown in the patent to Powell, et al, U.S. Pat. No. 6,129,687.

A Therapeutic Device for Treating Foot Pathologies is shown in the patent to Pepera, U.S. Pat. No. 6,499,485.

Another Therapeutic Device for Treating Foot Pathologies to Pepera is shown in U.S. Pat. No. 6,793,636.

More complex type of apparatuses can be seen in the Gymnastic Apparatus shown in the patent to Graham, No. 181,836.

An even more complex type of foot massager device is shown in the patent to Montague, U.S. Pat. No. 6,258,048, identified as an Electro/Mechanical Foot Massager.

A further complex device is shown in the patent to Mellor, No. 85,749.

Base type structures for foot massagers or exercising devices can be seen in the patent to Rocha, et al, U.S. Pat. No. 4,380,231, in their Foot Exerciser, as noted.

Finally, the patent to McKay shows another Foot Massager Apparatus, in U.S. Pat. No. 5,558,625.

SUMMARY OF THE INVENTION

This invention contemplates the formation of an apparatus for the treatment of plantar foot pain, to attain its lessening, and essentially is achieved through a removable roller that can be applied to a pivotal means; the roller essentially formed having an integral cavity that contains a freezable gel, which is designed to maintain a cool temperature during its continuous usage. The roller is pivotally applied to a stable base, which base may be formed of metal, a molded plastic, either of which may form the foundation for the apparatus, and the pivotal roller may be set within a cavity of the base, and extend slightly upwardly therefrom, so as to allow the cold temperature roller to biased against the undersurface of the foot, as it is moved forwardly and rearwardly, upon the device, for the treatment of the plantar area of the foot. Essentially, the removable roller may be formed of a somewhat flexible type of plastic, or even of a thin metal, but have sufficient rigidity so as not to collapse under the pressure of the foot, when used, but at the same time, have some resiliency so as to bias against the entire undersurface of the foot, as the foot is moved forwardly and rearwardly upon the roller, during its usage. The pivots at the end of the roller may include short pivot shafts, which fit within complementary slots formed at the end of the cavity formed within the base, so as to allow the roller to pivot therein, during usage. Or, the pivotal means may include a rod that extends through the entirety of the roller, in order to add more stability to the support of the roller, when mounted upon its base, and during its prolonged usage.

Stability for the base is essential to the proper operations of this device, and therefore, there may be frictional means provided upon the bottom of the base, that may engage and be held in position upon a floor, a rug, or any other means for support, and prevent the apparatus from shifting, during usage. Since the weight of the foot, and for that matter, the body, may be applied onto the roller, its stability when held within the base is essential, for the proper operations of this device.

It is, therefore, one of the primary objects of this invention to provide an apparatus that furnishes plantar foot treatment, through the provision of application cold therapy to the sole of the foot regardless of the surface where the user is sitting, or even standing, during its usage and application.

A further object of this invention is to provide a roller, applied to a base, which adds stability to its usage, as opposed to the usual rolling type of massagers, or dumbbells, as known in the art.

Another object of this invention is to provide a treatment device for the sole of the foot, that features a nonskid base which can be used on all household or recreational facility surfaces, including tile, carpet, hardwood, or concrete surface.

Still another object of this invention is to provide an apparatus for the treatment of the sole of the foot, through the usage of a refreezable roller that is secured in its base and one that prevents condensation or damage to any household surface.

Still another object of this invention is to provide a roller that incorporates a gel core, which is a form of refreezable roller, that provides many advantages over the freezing of water in a water bottle, or other related device, which can easily have a tendency to fracture or break, and eventually deposit water or other fluid over a household surface.

Still another object of this invention is to provide a roller fabricated from structural strength metal, or polymer, that will maintain its temperature over the treatment and have little risk of rupture as it is securely held in its base, even when subject to pressure from the foot during usage.

Yet another primary object of this invention is to develop an improved apparatus for delivering cold therapy to people suffering from plantar fasciitis and other common causes of plantar foot pain.

These and other objects may become more apparent to those skilled in the art upon review of the summary of the invention as provided herein, and upon undertaking a study of the description of its preferred embodiment, in view of the drawings.

DESCRIPTION OF THE PREFERRED EMBODIMENT

Figure 1:
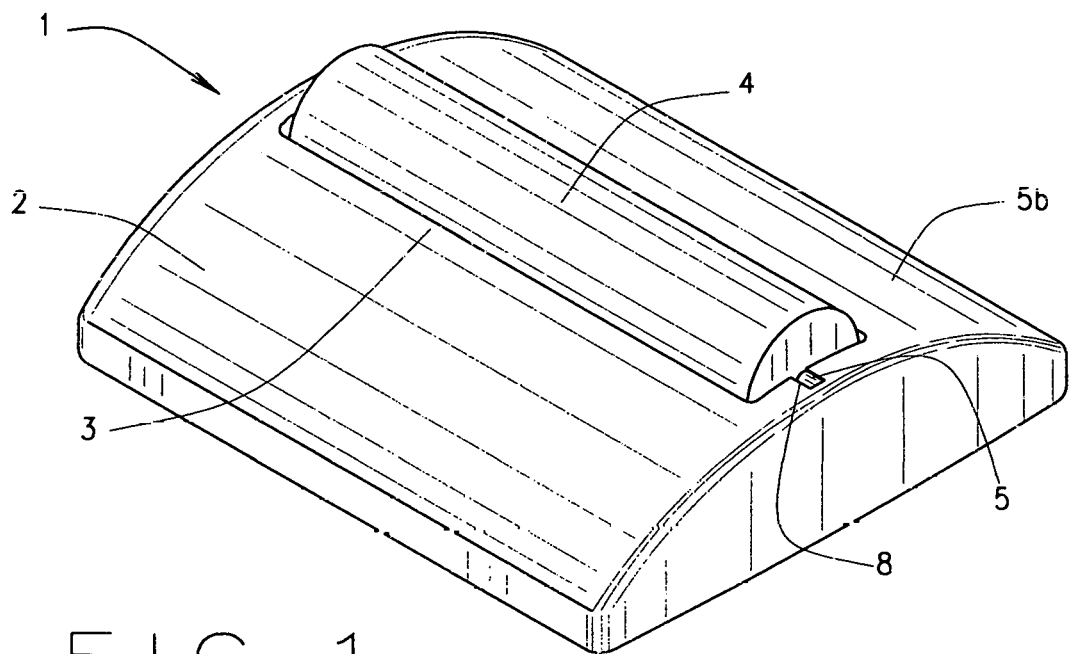
FIG. 1 is an isometric view of the Apparatus for Plantar Foot Pain Treatment of this invention.

In referring to the drawings, and in particular FIG. 1, therein is shown the apparatus 1 for plantar foot pain treatment. As noted, it generally includes a two part apparatus, the first part is the foundation or base 2, which contains, in its central upper portion, as at 3, a cavity for removably locating a freezable roller 4 that is pivotally mounted, through its pivot pins 5 upon the base, within its cavity or cradle 3, to provide a roller that contains freezable matter that the foot can rest upon, and move forwardly and rearwardly, upon the base, when subjecting plantar fasciitis to treatment. The pivot pins may form the ends of the rod 5a, as shown in FIG. 2.

Figure 2:
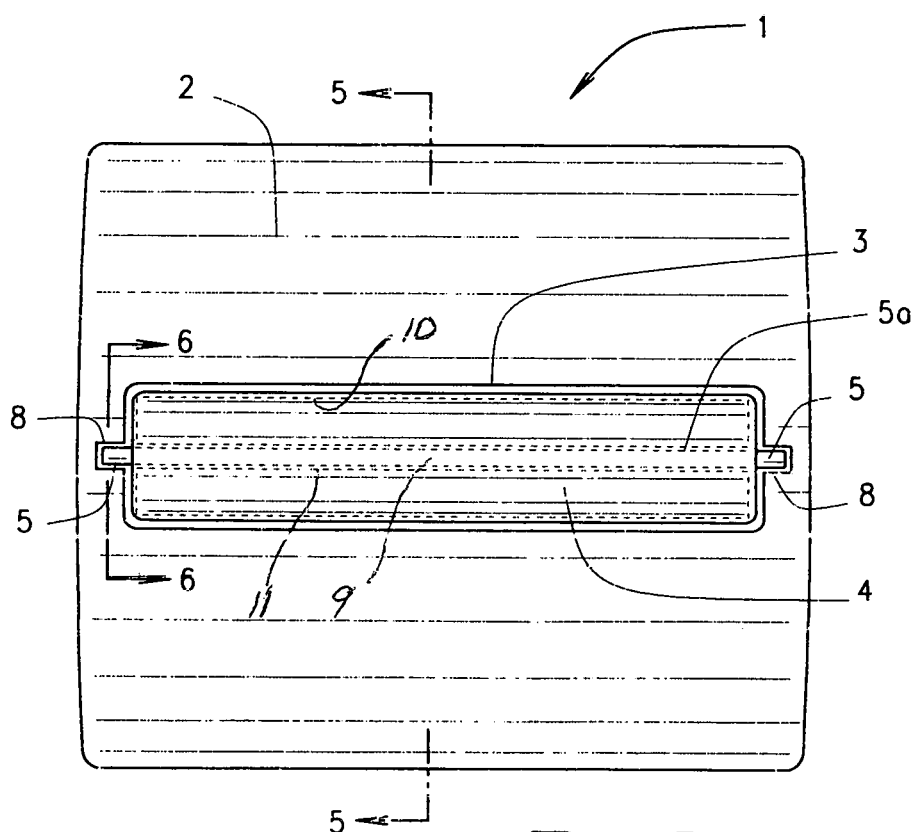
FIG. 2 is a top plan of the apparatus.

Generally, as can be seen in FIG. 2, the base is a more solid and stable component, having a lower surface 6 that can rest upon the floor, or any other base structure, and may include any type of nonskid material, whether it be downwardly extending serrations 7 as shown, a rubber type of nonskid material, or any other friction generating material that can be applied to the bottom of the base, to assure its stabilization and remaining in place, as the foot rolls upon the roller, during usage and application. A segment of the roller 4 extends upwardly, above the arcuate surface 5b of the base, so as to provide some degree of clearance for the foot, as it moves over the freezable roller 4, during its usage.

The base 2 may be fabricated of a molded plastic, to provide a foundation for the apparatus, or it may be formed of some type of metal, but preferably an injection or otherwise molded polymer that forms a stable base, which may further include some reinforcement therein, in order to make it structurally sound, to withstand the pressures of the foot, applying a force downwardly upon the freezable roller during its usage and application.

Figure 3:
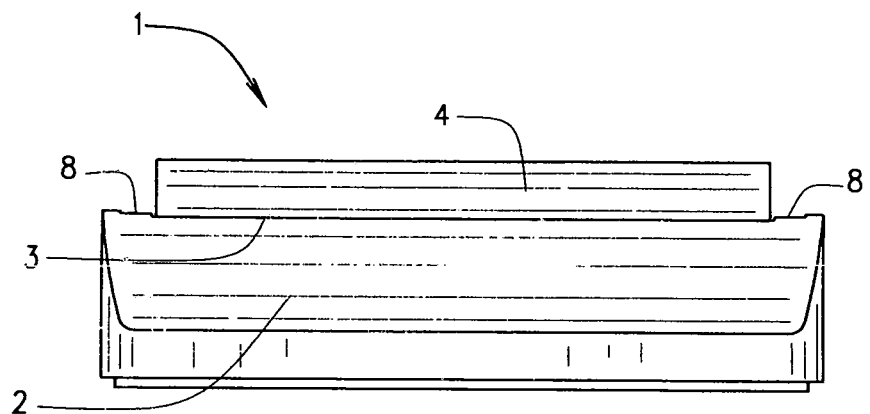
FIG. 3 is a front view of the apparatus.
Figure 5:
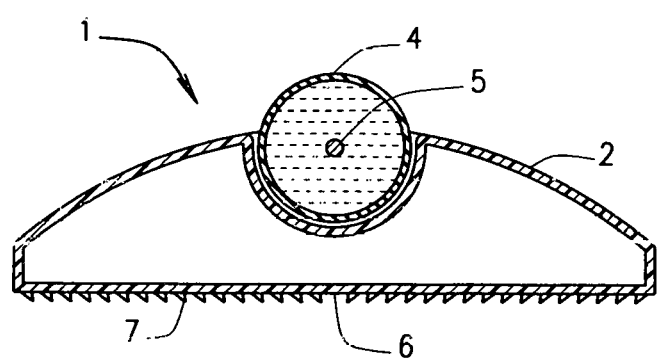
FIG. 5 is a sectional view through the apparatus taken along the line 5-5 of FIG. 2.

The roller 4 is more apply disclosed in FIG. 3, and FIG. 5, and includes its pivot pins 5 that extend lengthwise from the roller, in order to furnish the pivot points that rest within the slots 8 formed within the base, and designed for accommodating the pivot pins 5 therein, during usage of the device. To form the pivot pins, they may be either of a stub shaft design sticking out of the roller, or it may be a continuous length of metal rod, as at 9, that extends out of the ends of the formed roller, to form the pivot mechanism for the apparatus. This rod 9, as stated, may be continuous, and extends throughout the entire length of the freezable roller 4, where the ends of said rod, as at 5, form integral pivot pins for the roller when set within its foundation or base 2, as noted.

The removable roller itself may be formed of a polymer, having some degree of flexibility, but having sufficient stability so as not to collapse under the pressure of the foot, as the foot moves over the surface of the roller in a forward and aft direction of movement, during its usage. This may include any type of a injection molded polymer, that may be sealed at its ends to the rod 9, so as to provide a volumetric capacity therein, into which a freezable liquid or gel may be located, for use for the purposes of this invention. Or, the roller may be formed of a reasonably heavy film of polymer, which can yet be sealed to provide a fluidic seal of its liquid contents held therein, for prolonged usage and application. Said roller having an interior cavity.

As further provided within the roller 4, is a bladder, as at 10, and a bladder may have a central opening provided along its length, as at 11, so that the rod 9 may extend entirely therethrough, without breaking the seal of the bladder 10, with the ends of the rod, as at 5, providing the pivot pins for mounting within the apparatus base, during its application. It is this bladder that may contain the freezable liquid, or gel, and which is sealed within the roller 4, when the roller is subject to freezing, in preparation for application and usage. This bladder may be formed of any heavy sheet polymer material, such as polyethylene, polypropylene, or the like, that can be formed into a sealed bladder, for holding the freezable liquid or gel, permanently in place.

As previously reviewed, the type of liquid or gel that may be sealed therein, may extend anywhere from the range of a liquid, such as water, or preferably will be a form of heavy viscous type of gel, that can be frozen, to furnish the freezable roller for usage. Any type of additive that increases the viscosity of the fluid, to make it of a more gel like substance, will be preferred. Then, during usage, the roller simply can be lifted out of its cradle from the base, placed into a freezer, to allow for its gel contents to be frozen probably solid, and then placed back into the base, for ready application and usage by the patient.

Examples of the type of fluid, and viscosity agent, for forming a gel like material, may be as follows: Hydroxyethyl Cellulose, Polymer or Silica coated with vinyl.

In the usage and operation of this apparatus, prior to the use of the roller, with its internal cavity filled with a freezable gel, is placed in a household freezer for at least 120 minutes, to attain a solid freezing of its liquid content. When the user is ready to begin treatment, it removes the roller and aligns it into the nonskid base, more preferably within its cavity 3. At that point, the pivot pins of 5 will be located within their complementary base formed slots 8. From a seated position, the user will roll the sole of his/her foot on the cold roller for approximately 10 minutes. After use, the roller may be wiped clean and stored in the freezer for its next application. The invention, henceforth, provides a rapid, convenient method to treat common plantar foot injuries including plantar fasciitis.

Figure 4:
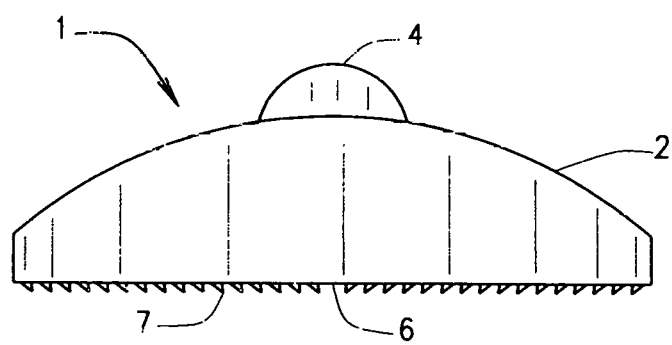
FIG. 4 is a side view thereof.
Figure 6:
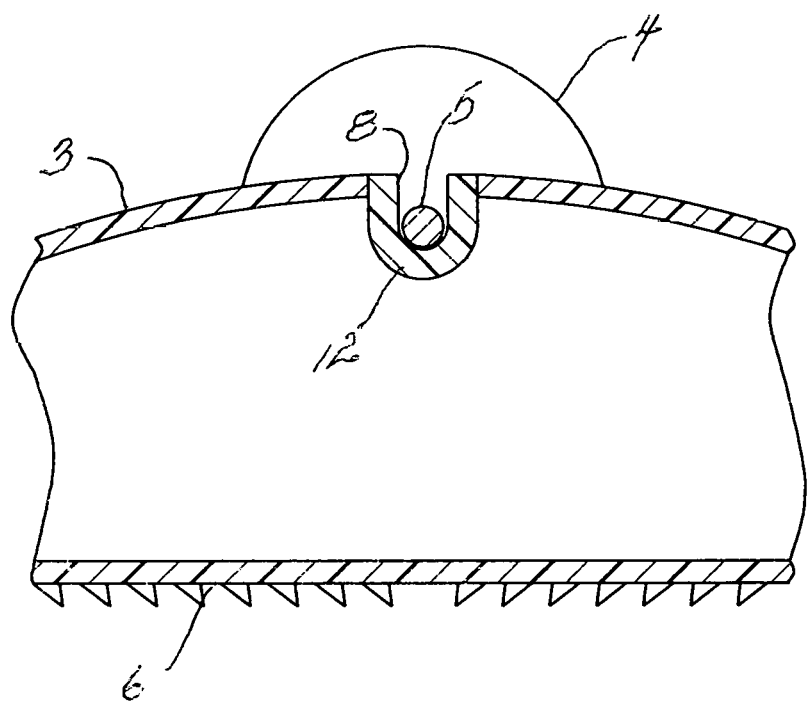
FIG. 6 is a partial sectional view showing the bearing surfaces where the pin of the roller rest during usage of the apparatus.

FIG. 6 shows a partial end view of the apparatus, showing its upper surface 3, the installed roller 4, and its frictional base or lower surface 6. As can be noted, the upper surface, in a position where the pivot pins 5 rest within their respective slot 8, the location of the slots is provided with U shaped bearing surfaces 12, so as to provide a reinforcement at the location where the roller sits, exerting its force upon the end pins 5, as they locate within the bearings 12, so as to be able to handle the heavy weight of the foot of the user, as it rolls upon the surface of the frozen roller 4, during application and usage in the treatment of plantar fasciitis, as previously summarized. FIG. 4 shows a true end view of the apparatus.

Also, to add reinforcement to the entire structure, the roller 4 may lie made of a stainless steel type of cylinder, to add to the strength of its usage, and the longevity of its application, in the prolonged treatment of those who suffer from plantar fasciitis, and seek a remedy, through usage of the apparatus of this invention.

Thus, it can be seen that the apparatus described to apply cold therapy is an easy to use, convenient means of treating common plantar foot pain. Cold therapy treatment is an established, commonly prescribed means of treating plantar fasciitis. This invention improves on any current devices, by providing a solid base type of nonskid surface, with a removable, reusable cold roller, that can be applied during the treatment process.

Variations or modifications to the subject matter of this invention may occur to those skilled in the art upon review of the invention as provided herein. Such variations, if within the spirit of this invention, are intended to be encompassed within the scope of any claims to patent protection issuing upon this invention. The description of the invention as set forth in the preferred embodiment, and its disclosure in the drawings, are set forth for illustrative purposes only.

We claim:

1. An apparatus for plantar foot pain treatment, including said apparatus having a base, said base having an under surface that rests stably upon a floor during its usage and application, the underside of said base has a frictional surface to prevent movement of the base during usage and application of the apparatus, said base having a contoured upper surface, said contoured upper surface of said base is substantially of an arcuate configuration, said upper surface at its upper most region having a cavity formed therein, said cavity forming a cradle, said cradle having ends and the cradle ends each having a slot formed therein, each slot having a semicircular bearing surface provided therein to provide reinforcement and accommodate the locating of a roller within the formed cradle, said roller provided for partially locating within said base cavity, and provided for rotatable movement therein, said roller being formed as a cylinder, and presenting a smooth outer surface for application of the user's foot thereupon during usage of the apparatus, said roller having an interior cavity, a freezable liquid pack provided within the roller and filling said roller's interior cavity throughout its extent, a pivot pin extends from each end of the roller, each pivot pin provided for locating within the slots formed adjacent the ends of the formed cavity to allow for rotation of the roller within said base during its usage, said freezable pack provided within the roller holding a freezable liquid permanently sealed therein, said freezable liquid comprising one of hydroxyethyl cellulose, a liquid polymer, or liquid silica coated with vinyl, and the freezable liquid having a viscosity agent added therein to form a gel like material, said roller forming a fluidic seal so as to permanently prevent leakage of any freezable liquid located therein, said roller being capable of removal from said base for deposit into a freezer to provide a solid refreezing of its freezable liquid contents, and then relocating said freezable roller into said base cavity in preparation for usage in treating foot pain, a rod extends through said formed roller and its freezable pack, said rod forming said pivot pins, the ends of the rod extend out the ends of the roller and the said freezable pack, and said pivot pins provided for locating of the freezable roller within the formed cavity of the base, and to provide for its rotation during usage and application, wherein said freezable pack has a central opening provided therethrough, and accommodating the location of the rod extending therethrough.

2. The apparatus of claim 1, wherein the base is formed of a molded polymer.

3. The apparatus of claim 1, wherein the base is formed of a metal.

4. The apparatus of claim 1, wherein the roller is formed of a metal.

5. The apparatus of claim 4, wherein the metal is stainless steel.

6. The apparatus of claim 1, wherein the roller is formed of a molded resilient plastic, and contains said freezable pack therein for holding said freezable liquid for use during treatment of the foot during application.

7. The apparatus of claim 1, wherein the frictional surface provided upon the underside of said base is a rubberized composition.

* * * * *